United States Patent
Sarkis et al.

[11] Patent Number: 5,921,933
[45] Date of Patent: Jul. 13, 1999

[54] MEDICAL DEVICES WITH ECHOGENIC COATINGS

[75] Inventors: Randall G. Sarkis, Chaska; Eileen L. Halverson, Blaine; Mark A. Tapsak, St. Anthony, all of Minn.

[73] Assignee: Medtronic, Inc., Minneapolis, Minn.

[21] Appl. No.: 09/135,468

[22] Filed: Aug. 17, 1998

[51] Int. Cl.⁶ ........................................... A61B 8/00
[52] U.S. Cl. ............................................ 600/459; 600/462
[58] Field of Search .................... 600/459, 461, 600/462, 464, 466, 467, 431, 433

[56] References Cited

U.S. PATENT DOCUMENTS

| | | |
|---|---|---|
| 4,219,886 | 8/1980 | Anderson .................................. 367/87 |
| 4,401,124 | 8/1983 | Guess et al. . |
| 5,081,997 | 1/1992 | Bosley, Jr. et al. . |
| 5,201,314 | 4/1993 | Bosley et al. . |
| 5,289,831 | 3/1994 | Bosley . |
| 5,327,891 | 7/1994 | Rammler . |
| 5,611,345 | 3/1997 | Hibbeln .................................. 600/461 |

*Primary Examiner*—Marvin M. Lateef
*Assistant Examiner*—Ali M. Imam
*Attorney, Agent, or Firm*—Reed A. Duthler; Harold R. Patton

[57] ABSTRACT

A medical device for insertion into human body having an echogenic portion of enhanced visibility in an ultrasound scan. The echogenic portion includes an echogenic material comprising a plastic impregnated with sonically reflective particles, the particles having an average size of less than 500 nanometers and formed of a substance having a specific gravity of 5 or greater. Preferably the particles have an average size of less than 100 nanometers and the sonically reflective particles are 5% to 40% of the echogenic material.

19 Claims, 5 Drawing Sheets

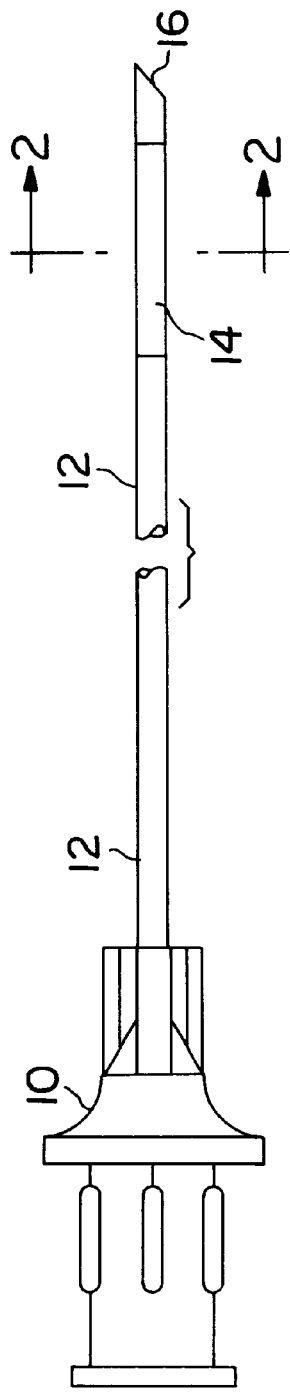
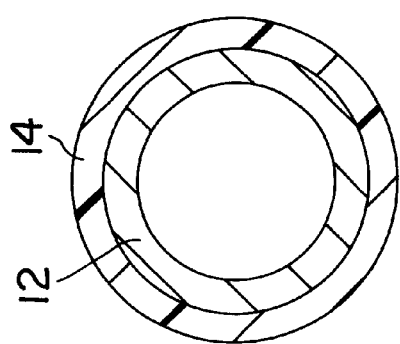

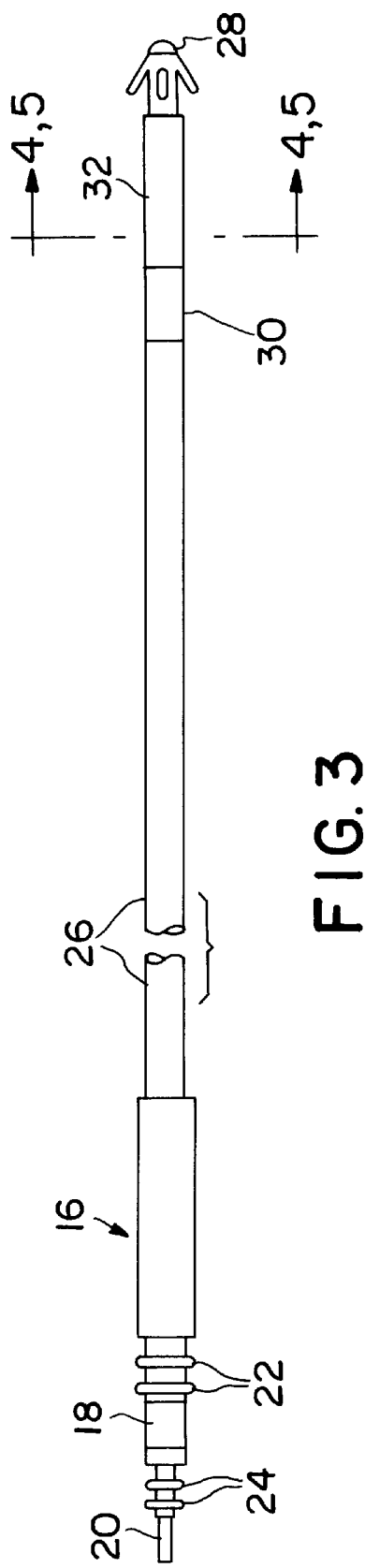
FIG. 3
FIG. 4
FIG. 5

MEDICAL DEVICES WITH ECHOGENIC COATINGS

BACKGROUND OF THE INVENTION

This invention relates generally to medical apparatus such as catheters, needles, electrode leads and other devices which are inserted into a patient's body and more particularly to the provision of echogenic coatings on such devices to enhance their visibility during ultrasonic imaging.

Ultrasonic imaging in the medical field is widely used for a variety of applications. In addition to imaging physiological structures and tissue such as organs, tumors, vessels, and the like, it is often desirable for a physician or technician to have an image of a medical device which has been inserted into the tissue or passageway of a patient. A variety of approaches have been used to enhance ultrasonic imaging of devices by increasing the acoustic reflection coefficient of the devices. In U.S. Pat. No. 4,401,124 issued to Guess et al., the reflection coefficient of a biopsy needle is enhanced by the use of a diffraction grating disposed on the surface of the needle. A variety of mechanisms for enhancing the ultrasound image of a portion of a medical instrument are also disclosed in U.S. Pat. No. 5,289,831 issued to Bosley, U.S. Pat. No. 5,201,314 issued to Bosley et al. and U.S. Pat. No. 5,081,997, also issued to Bosley et al. These patents disclose catheters and other devices provided with echogenic surfaces including spherical indentations or projections in the range of 0.5 to 100 microns or fabricated of material incorporating glass spheres or high density metal particles in the range of 0.5 to 100 microns. The use of micro-bubbles introduced into polymers to provide echogenic catheter components is described in U.S. Pat. No. 5,327,891, issued to Rammler.

SUMMARY OF THE INVENTION

The present invention is directed toward medical devices such catheters, biopsy needles, electrode leads, stents, dilators, cannulae and other medical devices employed within the human body which have enhanced ultrasound visibility by virtue of incorporation of an echogenic material. The material is fabricated by incorporating nanometer sized particles of sonically reflective materials, for example iron oxide, titanium oxide or zinc oxide into a biocompatible plastic. In one method of fabrication, the reflective particles are mixed with a powdered thermoplastic or thermosetting material such as a polyether amide, a polyurethane or an epoxy, or polyvinylchloridefollowed by thermal processing of the mixture to provide a material of increased sonic reflectance which may be applied as a coating on medical devices of the type discussed above or may be incorporated as a structural component of the medical devices. In a second method of fabrication, the reflective particles are mixed with a self curing polymer such as an epoxy or liquid silicone rubber, followed by curing the mixture in a mold or on or in a device component to provide an echogenic device component of the desired configuration.

By employing particles in the submicron range, preferably in the nanometer size range, a substantial amount of the sonically reflective material may be incorporated into the thermoplastic without significantly degrading its bulk properties or affecting its ability to be processed using conventional thermal processing techniques, including molding and extrusion. The use of particles in the nanometer range in particular allows for an increased degree of resolution of geometry of the device in an ultrasound scan. Average particle sizes are sub-micron, preferably less than 500 nanometers, more preferably in the tens of nanometers, for example 10–100 nanometers. In order to provide for a high degree of ultrasound visibility, and the particles are preferably formed of materials having a specific gravity greater than 5 and may be, for example, zinc oxide, iron oxide, titanium oxide or the like.

BRIEF DESCRIPTION OF THE DRAWINGS

FIG. 1 is a plan drawing of a biopsy needle in which the invention is practiced.

FIG. 2 is a cross section through the distal portion of the biopsy needle of FIG. 1.

FIG. 3 is a plan drawing of a medical electrode lead in which the present invention may be practiced.

FIGS. 4 and 5 are cross sections through the distal portion of the lead, showing alternate mechanisms by which the present invention may be incorporated into the lead.

DETAILED DESCRIPTION OF THE PREFERRED EMBODIMENTS

Figure 6:
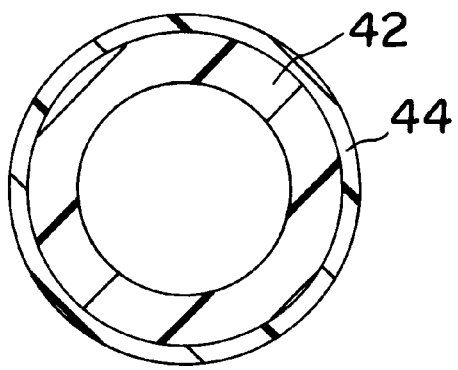
FIGS. 6, 7, 8 and 9 are cross-sections through catheter bodies incorporating the present invention.

FIG. 1 is a plan view of a biopsy needle incorporating the present invention. At the proximal end, the needle is provided with a plastic fitting 10, from which a stainless steel hollow needle 12 extends. Slightly distal to the sharpened distal tip 16 of the needle is a coating or sleeve 14 of echogenic material fabricated according to the present invention. The echogenic material, as discussed above, is fabricated of a plastic containing nanometer sized particles of material having a specific gravity of 5 or greater. The reflective material may either be applied to the needle as a coating, may be a molded or extruded sleeve, expanded and then shrunk around needle 12, extruded over needle 12 or adhesively bonded to needle 12 in order to maintain it in tight engagement with the surface of the needle. The needle may also be provided with a circumferential recess in which the sleeve or coating is applied. Alternatively, the thickness of the sleeve or coating may decrease at its proximal and distal ends to provide for a smooth outer surface. As yet an additional alternative, the coating or sleeve 14 may extend proximally all the way back to or closely adjacent to the distal end of fitting 10.

FIG. 2 illustrates the needle in cross-section in which the coating or sleeve 14 is applied over tubular needle 12. An appropriate thickness for the coating or sleeve may be, for example, 0.002 inches to 0.010 inches. The material may be fabricated according to the examples described below.

FIG. 3 is a plan view of an implantable electrode lead, in this case a cardiac pacing lead, in which the invention is employed. The lead is provided with a connector assembly 16 which carries a conductive connector ring 18 and a conductive connector pin 20. Sealing rings 22 and 24 assist in sealing the electrode lead in a corresponding connector block of an implantable medical device such as an implantable pacemaker, cardioverter or defibrillator. Extending distally from the connector assembly 16 is an elongated lead insulative lead body 26 which may be fabricated of polyurethane, silicone rubber or any of the various materials typically employed to manufacture implantable electrode leads. The lead carries electrode 28 at its distal tip coupled to connector pin 20 by means of a conductor within lead body 26 and a ring electrode 30 located proximal thereto and coupled to connector ring 18 by means of a conductor within lead body 26. The portion 32 of the lead between the ring electrode 30 and the tip electrode 28, typically referred to as a tip-ring spacer, is the portion of the lead having enhanced echogenicity according to the present invention.

FIG. 4 illustrates a cross-section through the tip-ring spacer 32 of a first embodiment of a lead according to FIG. 3. In this embodiment, this portion of the lead has a two layer structure comprising an inner polymer tube 38 and an outer polymer tube or sleeve 34, surrounding an internal coiled conductor 36 which couples tip electrode 28 to connector pin 20 (FIG. 3). In this embodiment, one of the inner tubular member 38 or the outer sleeve or coating 34 may be fabricated of a material according to the present invention, having increased echogenicity, with the other of the inner tubular member 38 fabricated of a biocompatible polymer such as polyurethane or silicone rubber.

FIG. 5 illustrates a cross-section through an alternative of an embodiment of a lead according to FIG. 3, employing the present invention. In this case, the tip-ring space region includes only a single extruded tubular member 40, fabricated of echogenic material according to the present invention, enclosing conductor coil 36. An additional, un-illustrated alternative would be to place the echogenic material in a lumen within the lead body.

Figure 7:
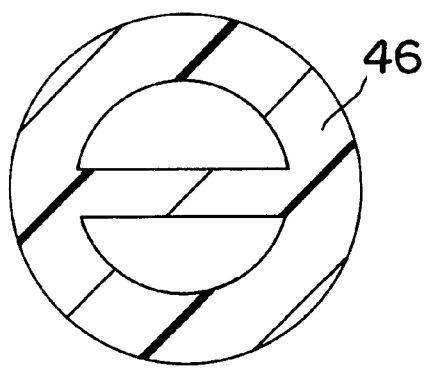
Figure 8:
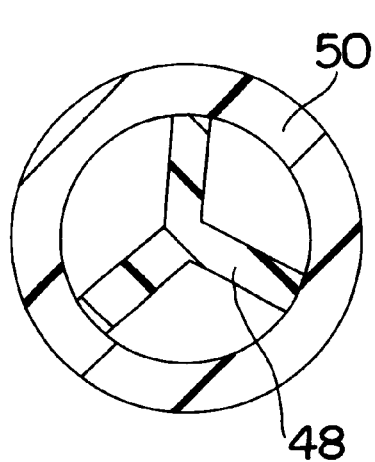
Figure 9:
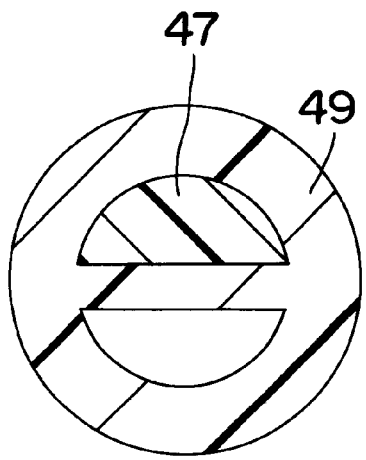

FIGS. 6, 7, 8 and 9 show alternative cross-sections through single and multi-lumen cannula or catheter bodies including echogenic materials fabricated according to the present invention. In FIG. 6, the catheter or cannula body is fabricated of an elongated tubular extrusion 42 surrounded by an outer sleeve or coating 44, either of which may be fabricated of echogenic material produced according to the present invention. FIG. 7 illustrates a cross-section of a multi-lumen cannula or catheter body, taking the form of an extruded bi-lumen tube 46, fabricated entirely of an echogenic material according to the present invention. FIG. 8 illustrates a two-piece multi-lumen catheter or cannula body fabricated having an inner, extruded, Y-shaped strut 48, surrounded by an outer extruded tube 50, either of which may be fabricated of an echogenic material produced according to the present invention. Figure illustrates a multi-lumen cannula or catheter body 49 fabricated of an extruded bi-lumen tube having an one lumen filled with an echogenic material 47 according to the present invention. The echogenic material 47 may be co-extruded extruded with the catheter or cannula body or may be inserted into as lumen of a previously formed catheter or cannula body.

Figure 10:
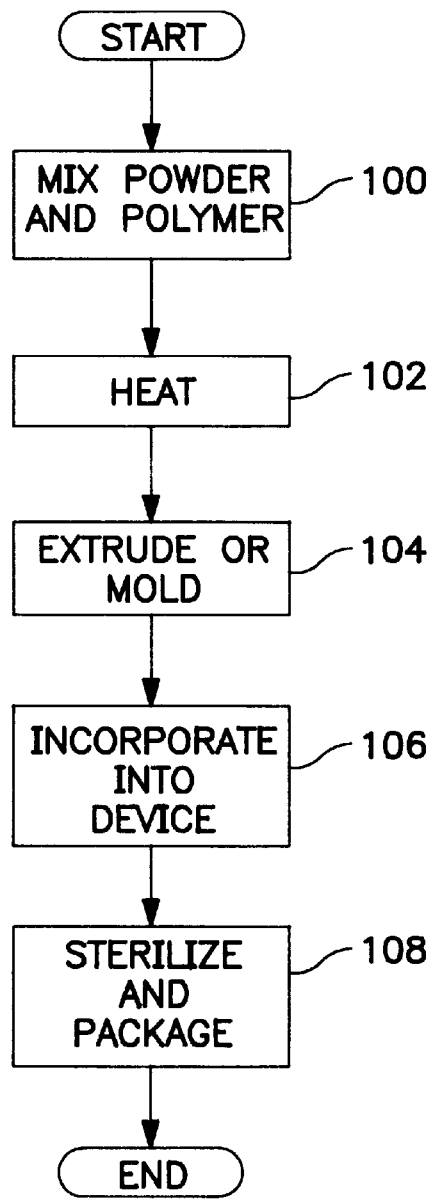
FIG. 10 is a functional flow chart illustrating a first process of manufacturing devices according to the present invention.

FIG. 10 is a functional flow chart illustrating one process of producing an single or multi-lumen tube, rod or other device component fabricated of an echogenic material according to the present invention. At 100, a desired thermoplastic resin in powdered or granular form is mixed with nanometer sized particles of a material having a specific gravity of 5 or more, such as iron oxide or zinc oxide. Additional materials appropriate for use in conjunction with the present invention include titanium oxide, silver oxide and platinum oxide. Appropriate thermoplastics include polyether amides, a polyether block amides, polyvinyl chlorides, polyurethanes and the like. Alternatively, a thermosetting resin such as an epoxy may be employed by mixing the particles with the liquid components of the resin. The resultant mixture is then thermally processed by heating at 102 and extruded and/or molded at 104 to form a tube, rod, sheet, or molded piece part. The resulting formed polymer is incorporated into the device at 106 and the device is thereafter sterilized and packaged at 108. Specific examples of materials so formed are set forth below.

Figure 11:
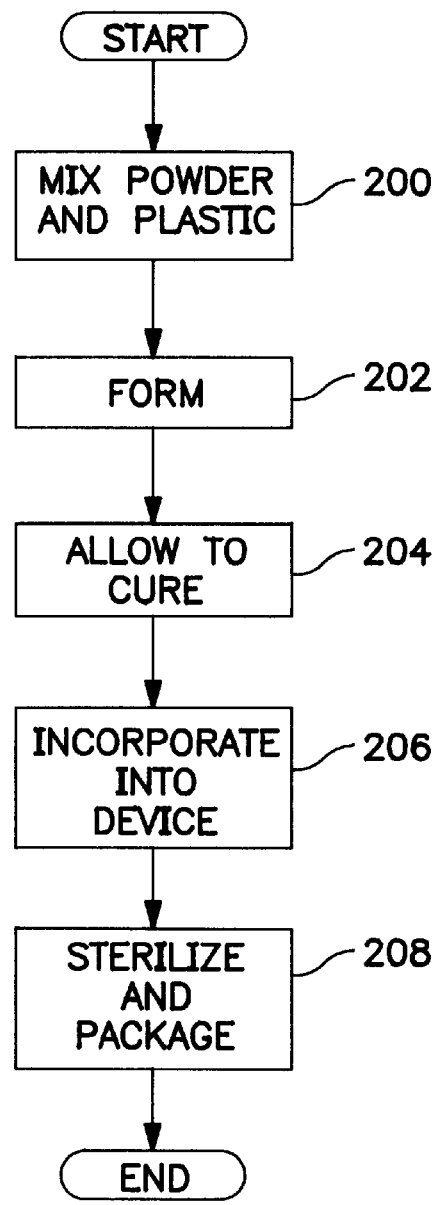
FIG. 11 is a functional flow chart illustrating a second process of manufacturing devices according to the present invention.

FIG. 11 is a functional flow chart illustrating the process of producing an medical device having a piece part or coating fabricated of an echogenic material according to the present invention using a plastic which cures at room temperature, such as liquid silicone rubber, epoxies and the like. At 200, the desired plastic resin in liquid form is mixed with nanometer sized particles of a material having a specific gravity of 5 or more, such as discussed above. The resultant mixture is then formed to display its desired physical configuration by being applied to the surface or interior of a component of the medical device or by being placed in a mold at 202 to form a tube, rod, sheet, or molded piece part and allowed to cure at 204. The resulting formed polymer is incorporated into the device at 206 and the device is thereafter sterilized and packaged at 208. Specific examples of materials so formed are also set forth below.

EXAMPLE 1

630 grams of powdered PEBAX® No 5533S01 polymer, a polyether block amide available from Elf-Atochem, may be placed in a polyester mesh bag and dried overnight in a desiccated air dryer operating at −40° F. dew point and at 170° F. To the dried PEBAX may be added 70 grams of NanoTek® zinc oxide having an average particle size of 36 nanometers, available from Nanophase Technology Corporation, Burridge, Ill. and the resulting blend may be mixed by tumbling. The PEBAX® polymer is suitable for molding and extrusion processes to produce piece parts and films, sheaths, filaments, tubes, sheets and the like. The resultant mixture may then be melt processed on a 34 millimeter twin screw Haake Rheocord Rheometer by slowly feeding the blend into the throat of the extruder. The extruder may be set to operate at 50 revolutions per minute, and the melt profile may be zone 1: 190° C., zone 2: 190° C., zone 3: 220° C. and final melt: 220° C. The polymer may be extruded directly into the form in which it will be incorporated into a medical device, for example, as a tube or rod, or may be subsequently processed by being chopped into pellets and employed in use in a subsequent extrusion process, molding process or other thermal processing technique. The material produced comprises 10% by weight zinc oxide and is readily extrudable.

EXAMPLE 2

As an alternative, 52 grams of the NanoTek® zinc oxide may be combined with 647.5 grams of the PEBAX® polymer, dried, mixed and thermally processed as described above. The material produced comprises 7.5% by weight zinc oxide and is readily extrudable.

EXAMPLE 3

Corresponding materials may be fabricated employing iron oxide, for example, NanoTek® iron oxide produced by Nanophase Technology, having a typical average particle size of 26 nanometers, may also be employed in like percentages and using like procedures to provide an echogenic coating or component for use in a medical device. Other sub-micron sized materials, preferably having specific gravities of 5 or greater, for example platinum oxide, titanium dioxide, silver oxide and the like, can be substituted for the iron oxide or zinc oxide.

EXAMPLES 4–6

Liquid silicone rubber may be mixed with the NanoTek® titanium dioxide powder having a average particle size of 20 nanometers in a 4:1 ratio by weight. The resulting mixture may be introduced into a tubular mold and allowed to cure at room temperature. Alternatively, Dupont TI-PURE® titanium dioxide having an average particle size of 340 nanometers, available from Dupont, Inc., Wilmington Del. or titanium dioxide powder having an average particle size of 25 nanometers, available from Degussa Corporation, Ridgefield N.J. may be blended in like quantities with liquid silicone rubber.

EXAMPLES 7–9

Liquid silicone rubber may be mixed with the NanoTek® zinc oxide powder having a average particle size of 20 nanometers in a 4:1 ratio by weight. The resulting mixture may be introduced into a tubular mold and allowed to cure at room temperature. Alternatively, zinc oxide powder having an average particle size of 450 nanometers, available from Aldrich Corp., Milwaukee, Wis. or zinc oxide powder having an average particle size of 310 nanometers, available from Strem Chemicals, Newburyport Mass. may be blended in like quantities with liquid silicone rubber.

In tests imaging tubes made according to examples 4–9 using a 7.5 megaherz ultrasound probe, it was observed that all samples were visible with adequate brightness. Further, in viewing the tubes with the probe held parallel to the axis of the tubes, the tubes made employing the smaller particles produced by Nanophase Corporation were visible with a higher degree of resolution, enabling both the near and far walls of the tubes to be visualized.

EXAMPLE 10

Any of the reflective powders referred to in Examples 4–9 may be mixed in like quantities with one or both of the hardener and resin of a two-part epoxy such as sold under the brand name HYSOL®, manufactured by the Dexter corporation, Windsor Locks, Conn. The mixture may be place in a mold or applied to the interior or exterior of a medical device component and allowed to cure.

Figure 12:
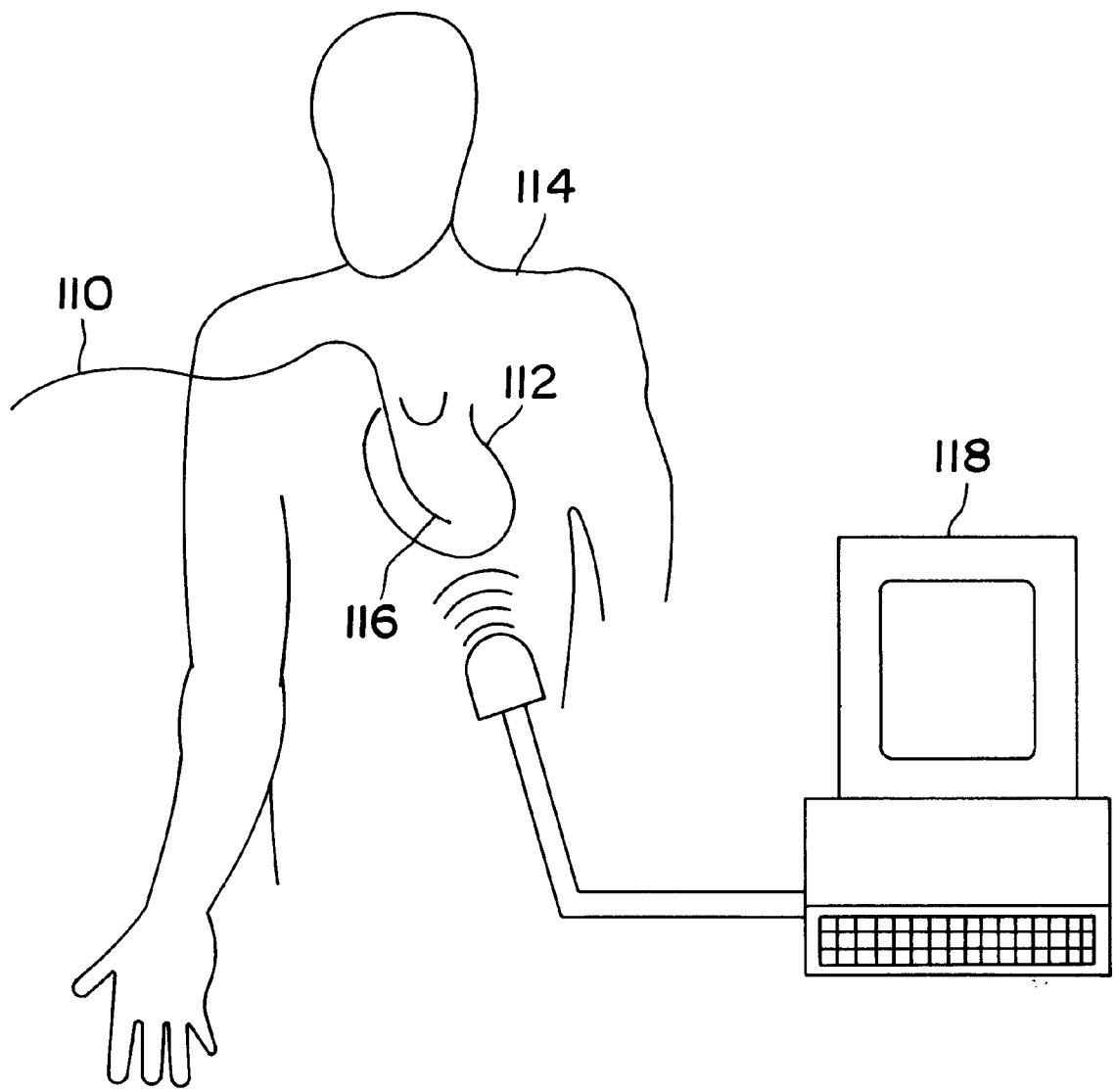
FIG. 12 is a diagram illustrating the use of the present invention to assist localization of a medical device inserted in a patient's body.

FIG. 12 illustrates the overall method of use of the device according to the present invention. In this case, a pacing lead 110 is shown being placed within the heart 112 of a patient 114 while being monitored ultrasonically. The distal portion 116 of the lead is provided with a coating of echogenic material or is fabricated of echogenic material according to the present invention, rendering it visible on ultrasound imaging system 118. The echogenic material according to the present invention may thus be usefully substituted for or used in addition to radiopaque materials typically employed to increase the fluoroscopic visibility of medical devices within the human body. Because ultrasound imaging systems are substantially less expensive than fluoroscopes and are available in clinics and hospitals worldwide where fluoroscopy may not be available, the fabrication of devices according to the present invention is believed to provide a substantial benefit both in reducing the costs associated with medical procedures employing the devices and increasing the number of physicians and facilities capable of employing the devices.

While the specific examples given above which employ the preferred nanometer sized sonically reflective particles employ particles having average particle sizes of 20, 26 and 36 nanometers, it is believed that other nanometer sized particles having average sizes less than 100 nanometers, preferably in the tens of nanometers, and preferably having a specific gravity of 5 or greater may be substituted for those specifically discussed above with similarly desirable results. Similarly, while the particles in the above examples comprised 7.5–20% of the weight of the materials, it is believed that materials constituting 2% to 40% by weight of sonically reflective particles may also be usefully employed. Therefore, the specific examples given above should be considered exemplary, rather than limiting, with regard to the claims which follow.

In conjunction with the above application, we claim:

1. A medical device for insertion into human body having an echogenic portion of enhanced visibility in an ultrasound scan, wherein the echogenic portion comprises:

an echogenic material comprising a plastic impregnated with ultrasonically reflective particles, the particles having an average size of less than 500 nanometers and formed of a substance having a specific gravity of 5 or greater.

2. A device according to claim 1 wherein the particles have an average size of less than 100 nanometers.

3. A medical device for insertion into human body having an echogenic portion of enhanced visibility in an ultrasound scan, wherein the echogenic portion comprises:

an echogenic material comprising a plastic impregnated with ultrasonically reflective particles, the particles having an average size of less than 100 nanometers.

4. A device according to claim 1 or claim 2 or claim 3 wherein the ultrasonically reflective particles are 5% to 40% by weight of the echogenic material.

5. A device according to claim 4 wherein the ultrasonically reflective particles are formed of zinc oxide.

6. A device according to claim 4 wherein the ultrasonically reflective particles are formed of iron oxide.

7. A device according to claim 4 wherein the ultrasonically reflective particles are formed of titanium dioxide.

8. A device according to claim 4 wherein the ultrasonically reflective particles are formed of platinum oxide.

9. A device according to claim 4 wherein the ultrasonically reflective particles are formed of silver oxide.

10. A device according to claim 1 or claim 3 wherein the plastic is a thermoplastic.

11. A device according to claim 10 wherein the plastic is a polyether block amide.

12. A device according to claim 1 or claim 3 wherein the plastic is an epoxy.

13. A device according to claim 1 or claim 3 wherein the plastic is self-curing.

14. A device according to claim 13 wherein the plastic is silicone rubber.

15. A device according to claim 1 or claim 3 wherein the plastic is a thermosetting plastic.

16. A device according to claim 1 or claim 3 wherein the device comprises an elongated needle provided with a sleeve or coating of said echogenic material.

17. A device according to claim 1 or claim 3 wherein said device comprises an elongated device body and wherein the echogenic material comprises a portion of the device body.

18. A device according to claim 1 or claim 3 wherein the device comprises an elongated device body, and wherein the echogenic material is applied to the exterior of the elongated device body.

19. A device according to claim 1 or claim 3 wherein said device comprises an elongated device body and wherein the echogenic material is located interior to the elongated body.

* * * * *